United States Patent [19]

Buschmann

[11] Patent Number: 5,241,300

[45] Date of Patent: Aug. 31, 1993

[54] SIDS DETECTION APPARATUS AND METHODS

[76] Inventor: Johannes Buschmann, Birkenleiten 9, 8000 München 90, Fed. Rep. of Germany

[21] Appl. No.: 874,297

[22] Filed: Apr. 24, 1992

[51] Int. Cl.⁵ ............................................. G08B 21/00
[52] U.S. Cl. .................................. 340/573; 128/721; 340/531; 340/600
[58] Field of Search .................... 340/573, 600, 531; 128/721

[56] References Cited

U.S. PATENT DOCUMENTS

| | | | |
|---|---|---|---|
| 3,517,999 | 6/1970 | Weaver | 128/721 |
| 4,169,462 | 10/1979 | Strubé | 128/721 |
| 5,088,501 | 2/1992 | Niewisch | 128/721 |

*Primary Examiner*—Glen R. Swann, III
*Attorney, Agent, or Firm*—Dominik, Stein, Saccocio, Reese, Colitz & Van Der Wall

[57] ABSTRACT

A transilluminated optical fiber is placed adjacent to an infant's respiratory moving parts using an elastic fabric. Use is made of the effect that moving the fiber causes a modulation of the intensity of the transmitted light to monitor the infant's breathing pattern to avoid S(udden) I(nfant) D(eath) S(yndrome).

19 Claims, 6 Drawing Sheets

SIDS DETECTION APPARATUS AND METHODS

BACKGROUND OF THE INVENTION

1. Field of the Invention

This invention relates to SIDS detection apparatus and methods and, more particularly, to monitoring the breathing of an infant through the use of an optical fiber that is in mechanical connection with an infant's chest and/or body and which shows a change of transmission when moved by respiratory chest movements.

2. Description of the Background Art

Sudden infant death syndrome, commonly called SIDS, also referred to as "cot death," is a sudden central respiratory arrest of still unknown origin. It represents a threat to virtually all infants in their first year of life. It has a mortality average rate of about 2 per 1000 ranging from 0.1 per 1,000 in Hong Kong to 5 per 1,000 in New Zealand (Deutsches Ärzteblatt 88, Heft 48, 28.11.1991). Therefore, it accounts for almost half of all deaths between the 2nd and 12th month of life. The reasons for the differences are again still unknown.

There are no pathological findings in the post-mortem examinations of the infants who die from SIDS. Furthermore, it is not possible to locate infants who are in particular danger. Striking correlations are the following: abdominal position, premature infants with muscular hypotonia, insufficient prenatal care, mothers with nicotine consumption during pregnancy, temperature of the infant's sleeping room, (Geburtshilfe und Frauenheilkunde 51, 1991,993).

In order to avoid the sudden infant death syndrome, there is only the uninterrupted long-term supervision of the infant in the dangerous time span between the 2nd and 12th month of life. Different approaches known from the state of the art include movement sensors which sense respiratory and/or cardiac actions, ECG-devices, impedance-pneumographs, induction plethysmographs, pulse oximeters, and the like.

Typical devices and methods found in the prior art are those disclosed in magazines and books of biomedicine or medical technology. The sensor-principles of devices available on the market are well known today. Innovations are usually related to artefact suppression.

Wherever chest electrodes are used, there is always the problem of electrical disconnection involved, leading to false alarms which frighten the parents or nurses as long as they are sensitive to the alarms. After a while those persons get less sensitive, which leads to an inflation of the alarm value.

Major problems occurring in all conventional monitoring processes are false alarms. False positive alarms (the device gives alarm while the infant is breathing normally), are triggered by sensors which lose contact, by disconnected cables and so on. False negative alarms (the device does not give alarm while the infant stopped breathing) come from devices whose alarm function has been switched off (reason false positive alarms) or because the sensitivity of the device is insufficient, and the like. Other problems are the annoying gluing or other means of fixing the sensors on the infant's body, high cost of sensors and devices.

The broad concept of an optical fiber to detect movement is disclosed in German Patent Number 39 28 635 A1 dated Aug. 26, 1989. There is no disclosure, however, of monitoring an illuminated optical fiber and initiating an alarm upon a stoppage of movement, and there is no disclosure of the use of optical fibers for medical purposes.

Therefore, it is an object of this invention to provide apparatus and methods which overcome the aforementioned inadequacies of the prior art and to provide improvements over the art.

It is further object of the present invention to provide an improved methods and apparatus for monitoring the respiration of an infant comprising, in combination optical fiber means located adjacent to the body of the infant to be monitored; means to transilluminate the fiber means; and means to monitor the transmission or transillumination as a function of the movement of the infant and of the fiber means.

It is the main object of the present invention to reliably detect when an infant stops breathing.

It is a further object of the present invention to monitor the breathing patterns and/or provide a continuous statistic evaluation of said breathing patterns of the infant and to actuate an alarm upon the occurrence of breathing stoppage.

The foregoing has outlined some of the more prominent features and applications of the intended invention. Many other beneficial results can be obtained by applying the disclosed invention in a different manner of modifying the invention within the scope of the disclosure. Accordingly, other objects and a fuller understanding of the invention may be had by referring to the summary of the invention and the detailed description of the disclosed embodiments in addition to the spirit and scope of the invention defined by the claims taken in conjunction with the accompanying drawings.

SUMMARY OF THE INVENTION

For the purpose of summarizing this invention, the invention may be incorporated into an improved a method of monitoring the respiration of an infant comprising the steps of placing optical fiber means adjacent to the respiratory parts of the infant to be monitored; transmitting light from a light source through the fiber means onto a photoelectric converter; monitoring changes in the intensity of the transmitted light as a function of the movement of the fiber means in response to the movement of respiratory parts of the infant; comparing changes in the intensity of transmitted light through movement of the fiber means corresponding to the infant's respiratory effects, with a predetermined threshold, indicating whether or not the infant is breathing; comparing the time elapsed since the last respiratory effect with a given maximum tolerable respiratory arrest time; and giving an alarm if the elapsed time exceeds the predetermined tolerable respiratory arrest time. The placing is effected by coupling at least a portion of the fiber means to a garment of the infant so as to be located on the chest/belly region of the infant and including the further step of clothing the infant with the fabric, whether a garment, elastic belt, adhesive tape, or the like.

The invention may also be incorporated into a method for monitoring the movement caused by the normal respiration of an infant and for triggering an alarm in response to the prolonged stoppage of such movement comprising the steps of placing an optical fiber means in a sinusoidal manner adjacent to the body of the infant to be monitored; establishing a tight contact of a garment containing the optical fiber by making use of an elastic fabric; transilluminating the fiber means with a light having a wavelength of between about 0.1 and 5 μm; monitoring the change of transmission of the fiber means with an evaluating electronic unit as a function of the movement of the fiber means as caused by the movement of the infant's respiratory part; and triggering an alarm upon the prolonged stoppage of the movement of the infant and the fiber means.

The alarm may be triggered adjacent to the evaluating electronic unit or remote from the evaluating electronic unit. The method may further include the steps of providing a separate remote alarm unit which triggers an alarm when an alarm signal is transmitted from the evaluating unit to the remote unit and may further include the step of transceiving a verification signal between the evaluating unit and the remote alarm.

The invention may further be incorporated into apparatus for monitoring the respiration of an infant comprising, in combination optical fiber means located adjacent to the body of the infant to be monitored; means to transilluminate the fiber means; and means to monitor the transillumination as a function of the movement of the infant and of the fiber means.

The apparatus further includes a garment with the fiber means woven into the garment so as to be located on the chest/belly region of the infant. The apparatus further includes an alarm and means to trigger the alarm as a function of the monitored transillumination. The apparatus may further include an evaluating electronic unit with a transmitter, and a separate remote portable alarm unit with an alarm and with means to initiate the alarm from a signal transmitted by the evaluating unit. The fiber means may be an optical monofilament or a bundle of fiber optic filaments. The material of the fibers may be silica, glass, plastic or the like. The alarm may be optical or accoustical. The signal may be infrared, ultrasound or radio wave. The apparatus further includes means associated with the evaluating unit and the remote alarm for transceiving therebetween a verification signal.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other methods and constructions for carrying out the same purposes of the present invention. It should also be realized by those skilled in the art that such equivalent methods and constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar numerals refer to similar parts throughout the various Figures.

DETAILED DESCRIPTION OF THE PREFERRED EMBODIMENT

SIDS is a common name for sudden infant death syndrome, a sudden central respiratory arrest which represents a threat to all infants in their first year of life with a mortality rate of about 1 out of 500. The reasons for this are unknown. Furthermore, it is not possible to identify infants who are in particular danger. In order to avoid the sudden infant death syndrome, there is only the uninterrupted long-term supervision of the infant. The present invention relates to an apparatus and methods for the extremely sensitive detection and reliable recording of respiratory movements. Due to its functioning, the method and device are very reliable and at the same time cost-efficient.

According to the invention, use is made of the effect that light in optical fibers shows a change of intensity when the fiber is moved, that is to say, it shows a change of the transmission of light through the fiber. There are two reasons for the change: (1) change in the conditions of propagation for modes if use is made of coherent light and (2) change in the geometry of total reflection within the fiber. In an unmoved fiber a fixed amount of light is transmitted through the fiber by means of total reflection. On the other hand, simultaneously a fixed amount of light leaves the fiber because the condition for total reflection is not met for all light paths, for example, at bendings, especially if light is fed into the fiber using almost the full maximum acceptance angle of the fiber. The maximum acceptance angle $2\alpha$ results from the numerical aperture NA of the fiber:

$$\sin \alpha = NA = \sqrt{n_1^2 - n_2^2}.$$

If the fiber is moved, then the geometry of the fiber is also changed; that is to say the angles of reflection in the fiber change with it. Total reflection may not be possible anymore where it has been before and vice versa. Thus a change in geometry changes the ratio of transmitted to lost light in the fiber. Only in an unmoved fiber will the conditions for total refection stay the same at every spot in the fiber. An additional change in transmission can be caused by a change of the overall length of the light path and the number of total reflections if the geometry of the fiber is changed, both altering the absorption of light. A further change in transmission results from a change of the cross section of the fiber which is slightly deformed during bending, the more the softer the material is of which the fiber is made.

These effects, very undesirable in communication technology but made of specific use here, can be optimized by a suitable choice of light, choice of fiber, and the coupling conditions for, thereby, detecting the motion of an infant's chest or belly.

In general, coherent light shows a higher sensitivity for bending than incoherent light. Also in general, fibers with a low numerical aperture exhibit a higher sensitivity for bending than fibers with high numerical aperture while monofilament fibers, in general, exhibit a higher sensitivity for bending than multimode fibers. Further, a plastic fiber showing more deformation of its cross section during bending than glass consequently exhibits again a higher sensitivity for bending. Lastly, feeding in the full acceptance angle results in a higher sensitivity for bending than feeding light far below the acceptance angle. With the use of semiconductor laser diodes, one can take advantage from both reasons for modulation in bent fibers. The use of light emitting diodes, LED's, on the other hand, is more cost effective.

Figures 1, 2:
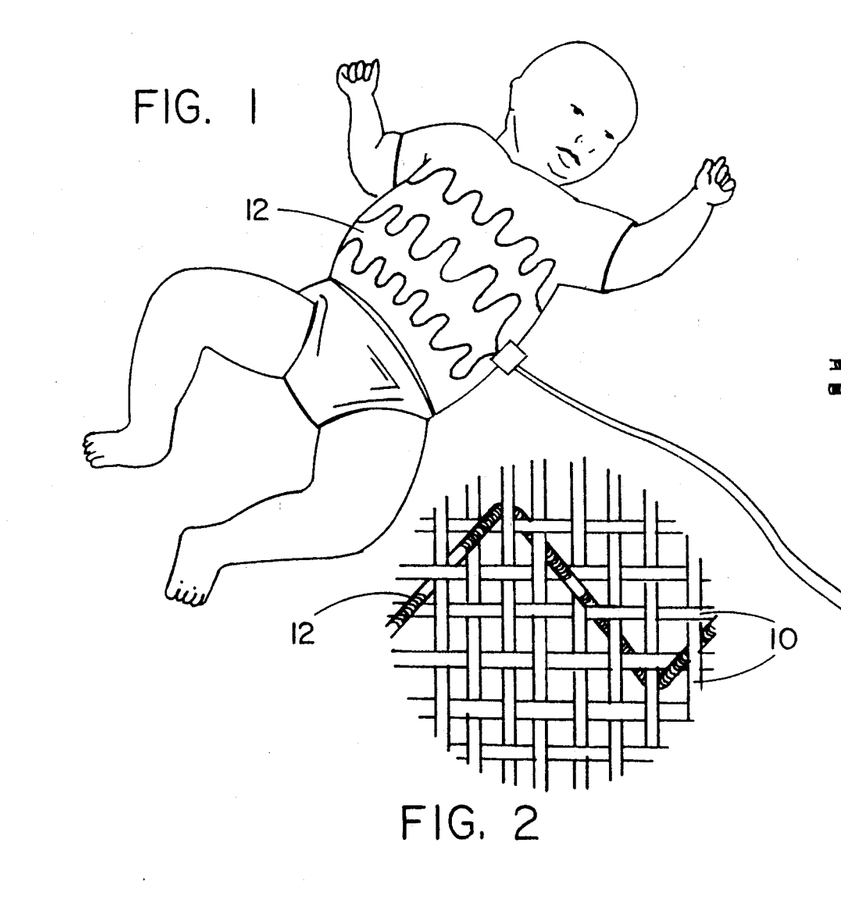
FIGS. 1, 2 and 3 illustrate an infant protected by an apparatus constructed in accordance with the principles of the present invention, with the fabric/optical fiber shown enlarged and with the connector also shown enlarged.
Figure 3:
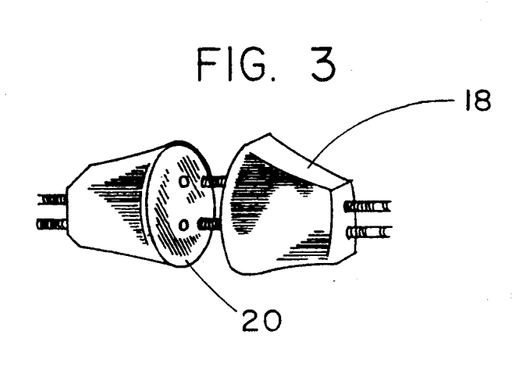

According to the preferred embodiment of the invention, a single optical fiber 10 is positioned in close contact with the infant's chest and/or belly. It is fabricated of a polymer such as PMMA (polymethylmethacrylic acid) or glass or silica, embedded in a thin polymer tube, as for example Tefzel which is a trademark of E. I. du Pont de Nemours of Wilmington, Del. The optical fiber has a diameter of about 30-150 μm. Flexibility of the fiber increases and possible bending radius decreases with decreasing fiber diameter. Transmission and light acceptance increase with the square of fiber diameter. It is woven into a shirt 12 or otherwise attached in a serpentine, sinusoidal or meanderlike manner to increase the length of the fiber in contact with moving parts of the infant. In this manner, the respiratory movements of the chest and/or belly lead to movements of the optical fiber.

Figure 4:
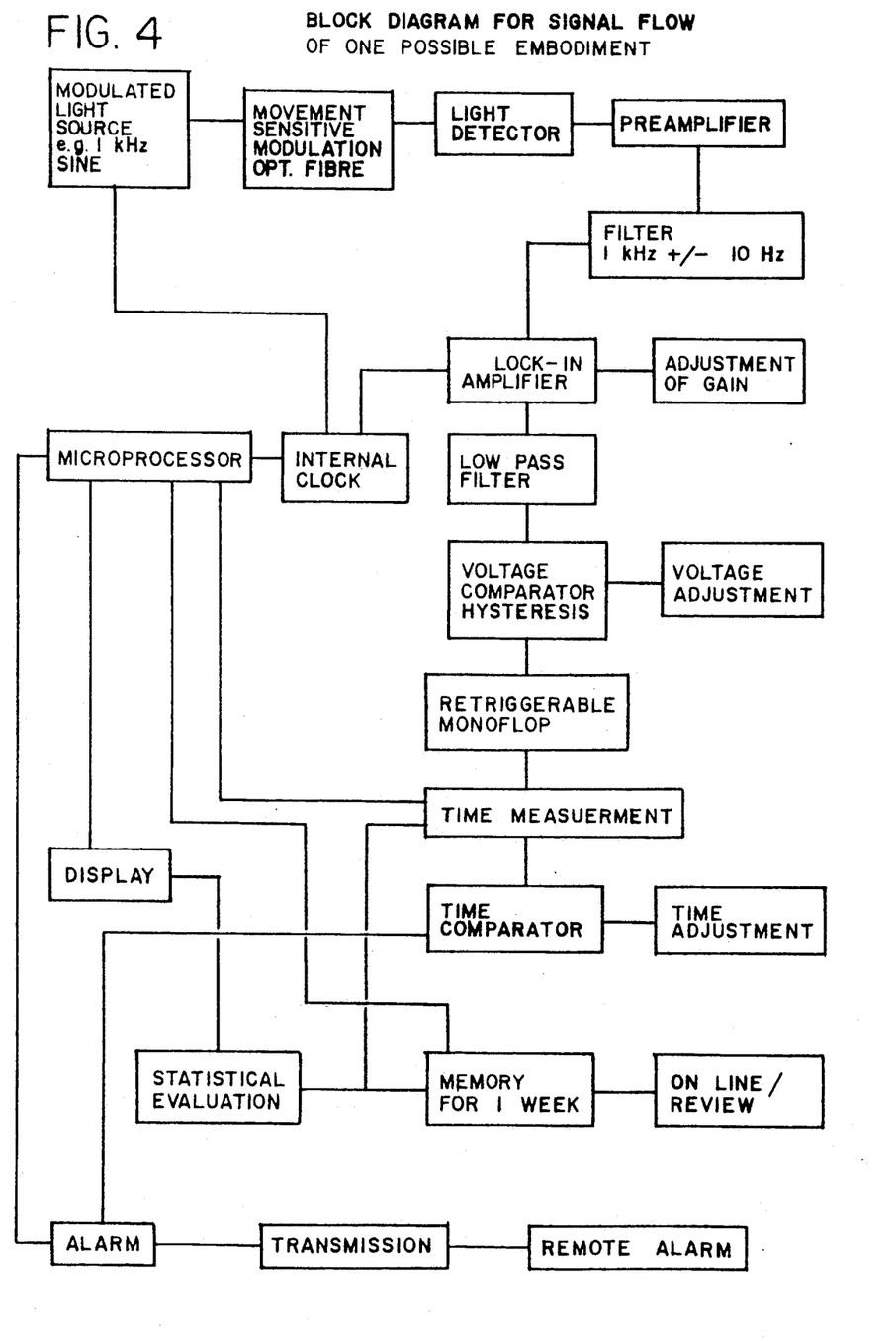
FIG. 4 shows a block diagram listing the signal flow and the steps of signal processing and the principal intrinsic logic of the apparatus and method.
Figure 5:
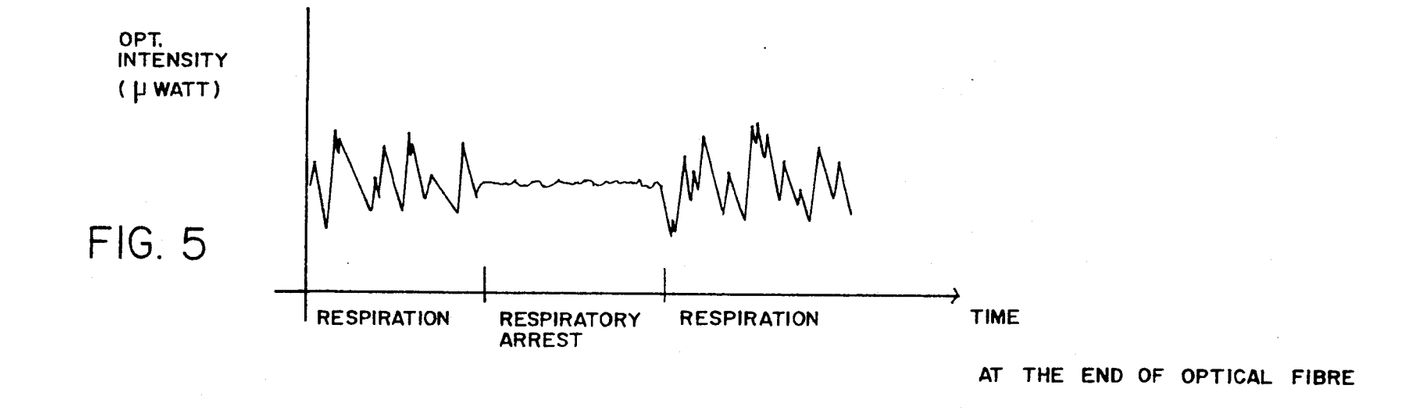
FIG. 5 shows the signal at the end of the fiber: the light intensity versus time wherein during the respiratory movements, a light intensity noise occurs.
Figure 6:
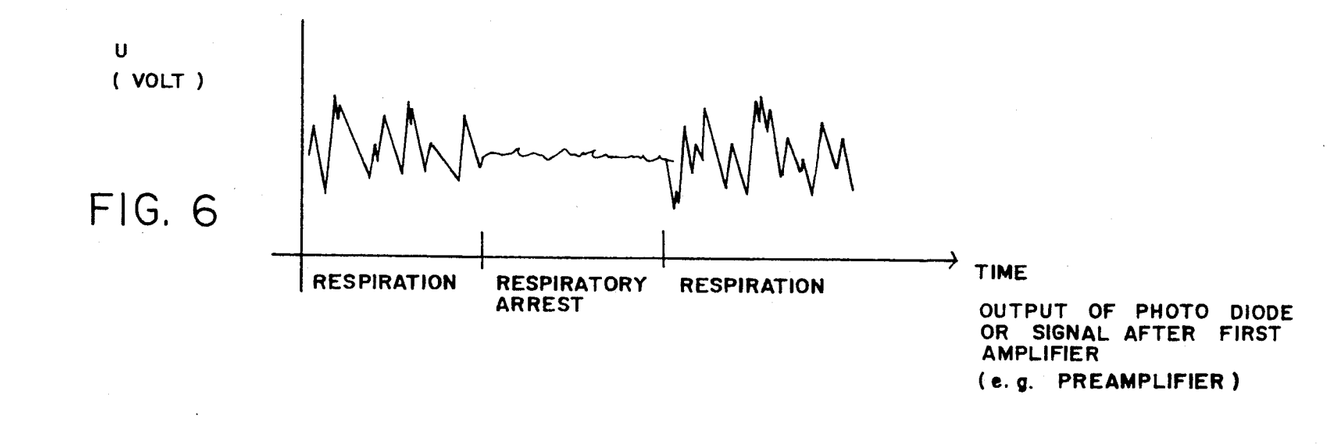
FIG. 6 shows the signal at the photodiode or at the end of the preamplifier (current to voltage converter): the voltage versus time wherein during the respiratory movements, a current (voltage) noise occurs related to the light intensity noise.
Figure 7:
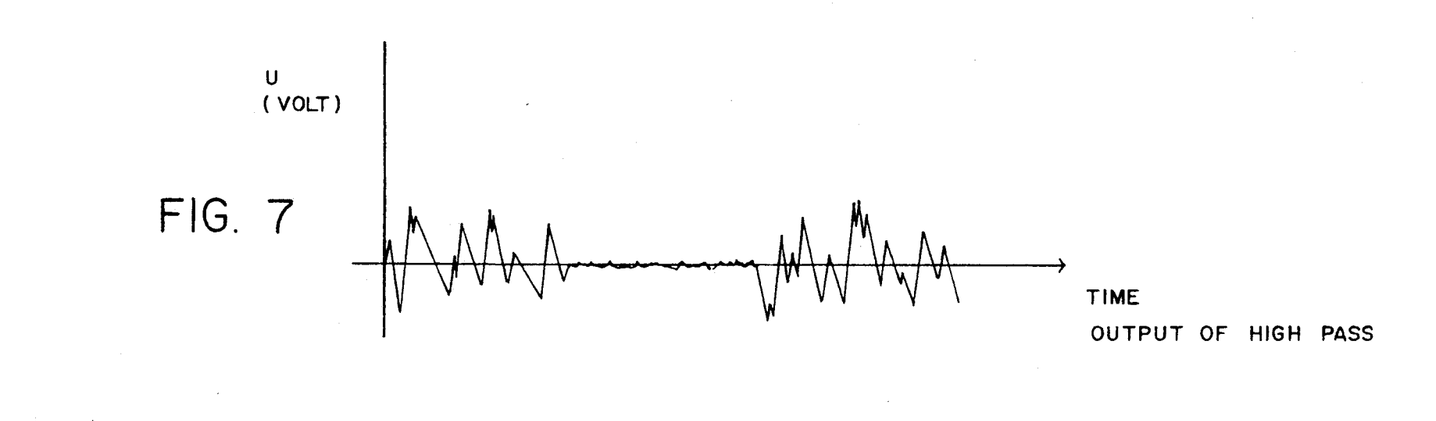
FIG. 7 shows the signal after a high pass: the voltage versus time wherein the DC (direct current) component has been removed.
Figure 8:
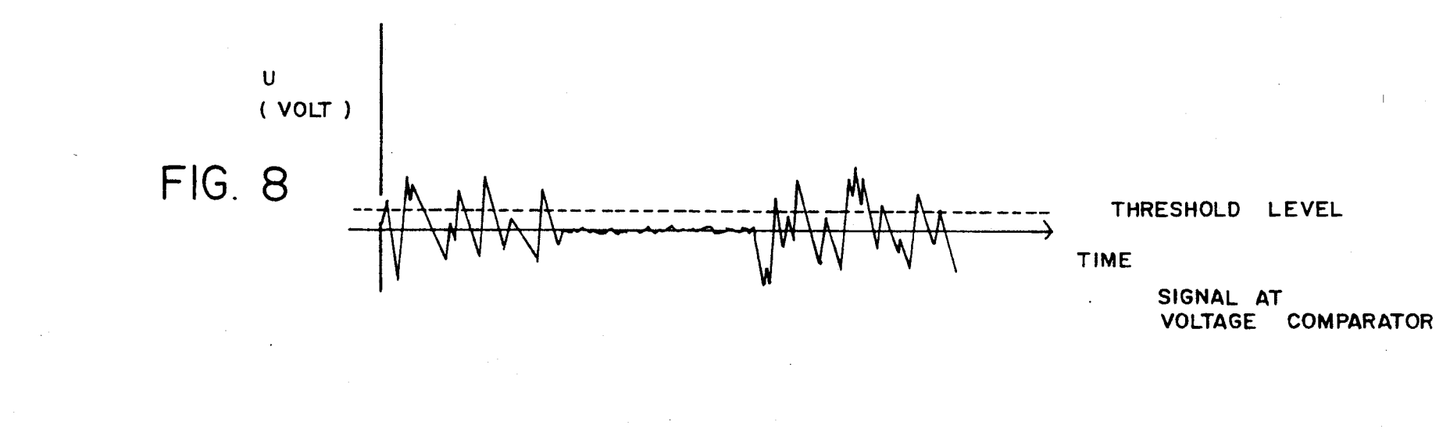
FIG. 8 shows the signal and the threshold level in the voltage comparator: the output voltage versus time wherein the noise exceeds the threshold level during respiratory movements.

As described above, these movements cause noise type modifications of the transmission of light in the fiber. To accomplish this, light from a suitable light source (e.g. an LED) is coupled to one end of the optical fiber 10 and at the end the fiber is directed onto a photodetector (e.g. a photodiode). This photodetector, receiving the transmitted light, converts this noise from an optical signal into an electric signal which is amplified and sent through a high pass and a low pass (band pass) filter (AC coupling). In this respect, it is useful to choose a suitable frequency band preferably between about 0.1 and 10 Hz, in order to reduce external influences caused by artificial light such as fluorescent tubes, or couplings of the line frequency, and to extract the small changes in intensity compared with the overall light intensity exhibited by the signal to be used. The changes of transmission in the frequency band occur during respiratory excursions. If the AC (alternating current) signal corresponding to the transmission noise exceeds a predetermined and/or adjustable threshold, a sufficient respiratory effect (movement) is assumed. To become even more independent of ambient light, the light source can be modulated with a frequency far above the highest naturally occurring frequency of light modulation (120 Hz fluorescent tubes), for example 1 to 10 kHz. In this case, after transmission through the fiber, there could be demodulating means for extracting the said frequency band of about 0.1 to 10 Hz.

Thus the suitable monitoring device or electronic evaluation unit 16 monitors the respiration of the infant and triggers an alarm if the respiration stops for a longer period than a suitable time interval. Such suitable time interval can be selected and varied by either the manufacturer, the doctor or parent through a control dial. If the breathing stops for a longer time than the adjusted time interval, an alarm is triggered. According to the invention, the alarm is given either as a signal, either acoustic or optical, at the location of the evaluation unit or via a transmission to a remote alarm device. The evaluation unit could also provide a statistic analysis for example by making use of multiple bar-graph-displays which assemble horizontally different classes of time intervals between the respiratory movements and vertically the frequency with which the classes occur.

In order to make the use of the monitoring device as practical as possible, it is important that the shirt or other garment, which may include elastic threads and which contains the optical fiber, can easily be disconnected from the connecting cables, or as the case may be, from the electronic evaluation unit. Therefore, according to the invention, there is a closed loop consisting of a light source in the apparatus, for example a LED, a connecting cable bringing the light from the source to an optical plug 18, 20 at the infant's shirt which can be connected and disconnected travelling through a thin optical fibre 12 that is woven into the fabric 10 of the infant's shirt, being in mechanical contact with moving parts of the infant's body, back through the optical plug and the connecting cable to the device and onto a photodetector. By means of the plug, the shirt can be changed easily for cleaning. The coupling is effected either by direct end-to-end contact of the fibers or by using optical parts like lenses or graded index rod lenses.

Figures 1A, 2A, 3A:
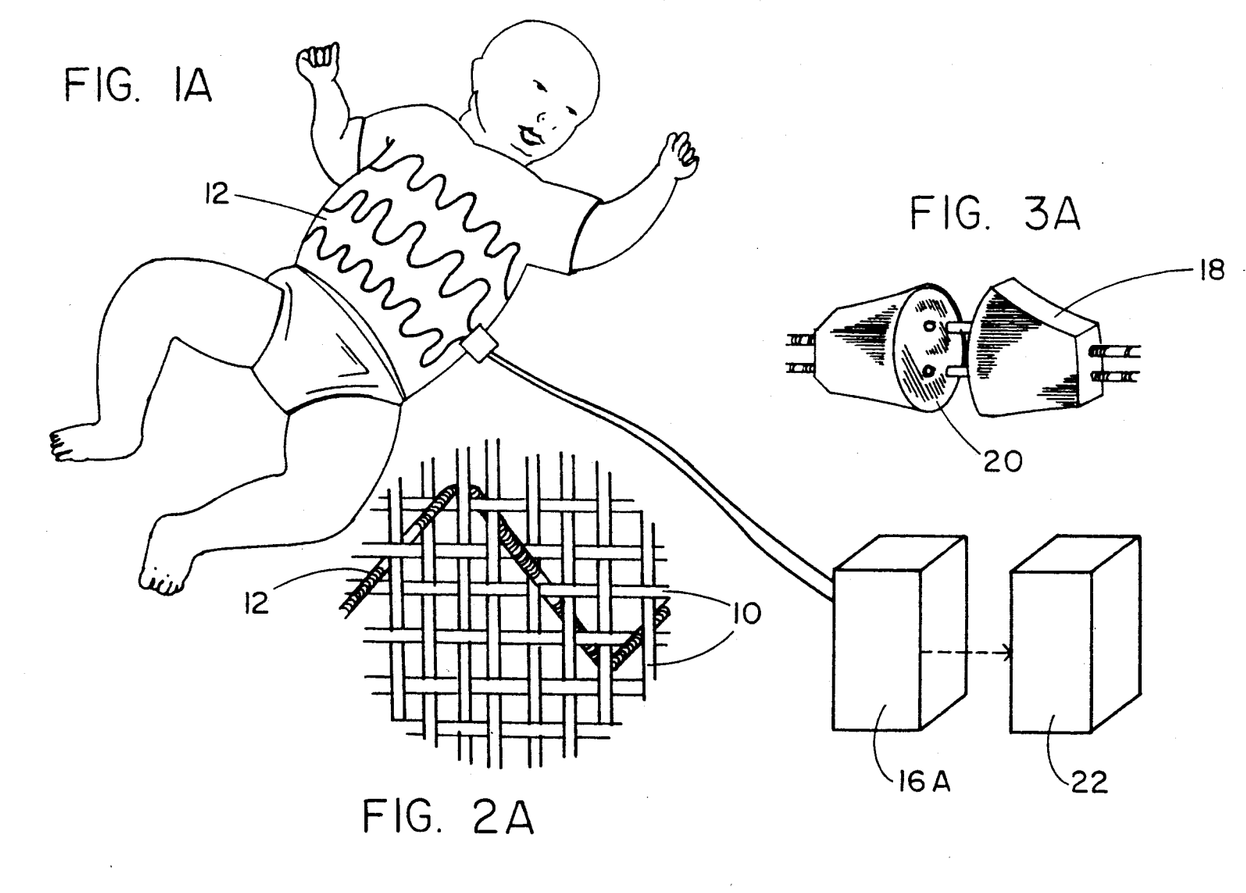
FIGS. 1A, 2A and 3A are similar to FIGS. 1, 2 and 3 but illustrate an alternate embodiment of the invention, and with the fabric/optical fiber shown enlarged and with the connector also shown enlarged.

An alternate embodiment of the alarm unit of the device includes a remote alarm unit 22, a small portable additional signal unit, battery powered, which is fixed at the parent's or nurse's clothing or other location adjacent to the parent or nurse's, receiving a signal from the main alarm unit by infrared (like TV remote control, for use within short ranges) or radio transmission (like wireless telephone for longer distances). It is adapted to receive signals transmitted from the electronic unit 16A adjacent to the infant. To ensure that an alarm can be transmitted any time and anywhere, the control device could send a continuous unmodulated carrier frequency to the remote alarm unit which gives an alarm either when the unmodulated carrier cannot be received indicating lost contact with the control device or when the carrier is modulated indicating a respiratory arrest, both of the alarms being different to be distinguishable. Another way of ensuring correct transmission of the alarm signal would be the exchange of verification signals between the control unit and the remote alarm unit exchanged either continuously or discontinuously. This is to verify and ensure that an alarm can be transmitted in the above described manner. The main microprocessor, the control device, with its signal transmitter, and the remote alarm with its signal receiver, are each provided with components to transmit and receive a verification signal to test that the signal transmitter and signal receiver are functioning properly for the transmission of signals if transmitted. Such verification signal could be continuous or it may be intermittent over short, predetermined time intervals for appropriate testing and verification of operation of the system.

The device is a box comprising:

(a) a power supply and/or (rechargeable) battery, (b) a light source; i.e. a light (also ultraviolet and infrared are called "light" in this disclosure) emitter preferably a LED with 660 nm center wavelength, so that the human eye can control the light visually, (c) a light receiver preferably a photodiode, (d) a preamplifier, (e) a high and low pass (band) pass filter, (f) an amplifier, (g) a voltage comparator deciding whether the noise exceeds a predetermined threshold, (h) a clock generating processing paces for the microprocessor and time intervals for comparison with time intervals between respiratory efforts, (i) a microprocessor, (j) an alarm unit, and/or a remote alarm unit, and (k) a display for showing statistical data of respiration patterns.

Additionally the monitoring system comprises:

(a) a connector for connecting the optical fibers of the connecting cable and of the shirt and (b) an exchangeable infant's shirt or garment into which an optical fiber is woven.

Figures 9, 10, 11:
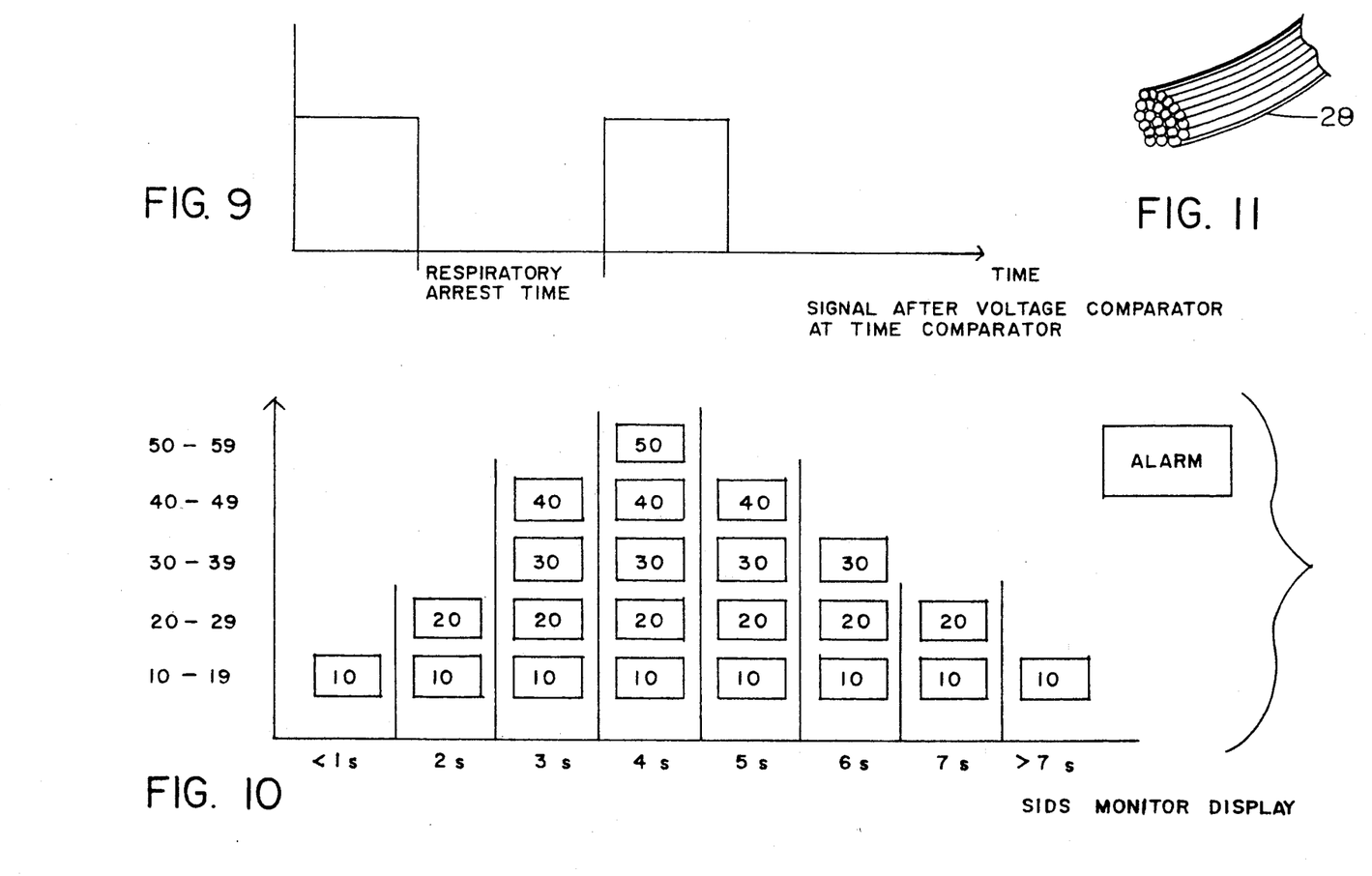
FIG. 9 shows the output signal of the voltage comparator: the output voltage versus time wherein the bistable comparator provides a high output when respiratory movements occur and a low output when respiratory arrest occurs or vice versa.
FIG. 10 illustrates a preferred embodiment of a statistic display.
FIG. 11 illustrates a fiber optics bundle constructed with the alternate embodiment of the invention.

In an alternate embodiment of the invention, that is shown in FIG. 11, the monofilament optical fiber is replaced by a plurality of optical fibers 28 which could, for example, be coupled together by, or embedded in, a transparent adhesive to form a bundle of filament instead of the monofilament optical fiber of the primary embodiment. The filaments are preferably of a diameter of 30–50 μm with about 30–1,000 filaments per bundle.

The device contains an alarm which is activated if the infant's respiration ceases for a period of time exceeding a predetermined internally set value or an externally adjustable value. In this case, optical transmission noise, converted into an electrical noise, falls below a predetermined intensity internally set, too. The alarm can be either optical or acoustical, either at the site of the device or remote by making use of an additional portable remote alarm unit. Such portable remote alarm unit also receives its information by making use of radio waves sent to the portable remote alarm unit at another convenient location for the parent or other person charged with monitoring the infant.

As it is possible that a disposition to SIDS exists, a documentation of occurrences of insufficient breathing can be interesting and desirable. Therefore, the device may be equipped with a semiconductor memory and/or an attachable printer in order to document these occurrences. Said memory could be located on a removable memory card that could be taken to the hospital for evaluation without making it necessary to transport the entire unit. In the meantime the circuit can continue storing the data on another memory card.

There are classes of the time elapsed between respiratory efforts or time after last respiratory effort and also classes of frequencies. A certain class and frequency is represented; e.g. by a bright LED, lit when a class if full. Note FIG. 10. If in one class of elapsed time a class of the highest frequency is full, and the same time class occurs again, all the other time classes have to be reduced in frequency. This leads to a spectrum of frequencies revealing the statistical breathing pattern of the infant monitored.

In operation and use, the present invention contemplates a method for monitoring the movement caused by the normal respiration of an infant and for triggering an alarm in response to the prolonged stoppage of such movement. The method includes the step of placing an optical fiber means in a sinusoidal manner adjacent to the respiratory parts of the infant to be monitored. A tight contact is established by a garment, belt, tape or the like containing the optical fiber by making use of an elastic fabric. The method also includes the step of transmitting light from a light source through the fiber means onto a photoelectric converter thereby transilluminating the fiber means with a light having a wave length of between 0.1 and 5 μm. Changes in the intensity of the transmitted light are monitored as a function of the movement of the fiber means in response to the movement of the respiratory parts of the infant. Changes are compared in the intensity of the transmitted light through movement of the fiber means corresponding to the infant's respiratory effects, with a predetermined threshold, indicating whether or not the infant is breathing. The time elapsed since the last respiratory effect is compared with a given maximum tolerable respiratory arrested time. The method also includes the step of triggering an alarm upon the prolonged stoppage of the movement of the infant and the fiber means.

In carrying out the method, the alarm may be triggered by an evaluating electronic unit adjacent to the infant. In the alternative, a separate remote alarm unit may be provided which triggers the alarm at the remote unit when an alarm signal is transmitted from the evaluating unit. In such circumstances, the method includes the step of transmitting a verification signal between the evaluating unit and remote alarm.

The present disclosure includes that contained in the appended claims, as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

Now that the invention has been described, What we claim is:

1. A method of monitoring the respiration of an infant comprising the steps of:

placing optical fiber means adjacent to the respiratory parts of the infant to be monitored;

transmitting light from a light source through the fiber means onto a photoelectric converter;

monitoring changes in the intensity of the transmitted light as a function of the movement of the fiber means in response to the movement of respiratory parts of the infant;

comparing changes in the intensity of transmitted light through movement of the fiber means corresponding to the infant's respiratory effects, with a predetermined threshold, indicating whether or not the infant is breathing;

comparing the time elapsed since the last respiratory effect with a given maximum tolerable respiratory arrest time; and giving an alarm if the elapsed time exceeds the predetermined tolerable respiratory arrest time.

2. The method as set forth in claim 1 wherein the placing is effected by coupling at least a portion of the fiber means to a garment of the infant so as to be located on the chest/belly region of the infant and including the further step of clothing the infant with the garment.

3. A method for monitoring the movement caused by the normal respiration of an infant and for triggering an alarm in response to the prolonged stoppage of such movement comprising the steps of:

placing an optical fiber means in a sinusoidal manner adjacent to the body of the infant to be monitored;

establishing a tight contact of a garment containing the optical fiber by making use of an elastic fabric;

transilluminating the fiber means with a light having a wavelength of between about 0.1 and 5 $\mu m$;

monitoring the change of transmission of the fiber means with an evaluating electronic unit as a function of the movement of the fiber means as caused by the movement of the infant's respiratory part; and triggering an alarm upon the prolonged stoppage of the movement of the infant and the fiber means.

4. The method as set forth in claim 3 wherein the alarm is triggered adjacent to the evaluating electronic unit.

5. The method as set forth in claim 3 wherein the alarm is triggered remote from the evaluating electronic unit.

6. The method as set forth in claim 3 and further including the steps of providing a separate remote alarm unit which triggers an alarm when an alarm signal is transmitted from the evaluating unit to the remote unit.

7. The method as set forth in claim 6 and further including the step of transceiving a verification signal between the evaluating unit and the remote alarm.

8. Apparatus for monitoring the respiration of an infant comprising, in combination:

optical fiber means located adjacent to the body of the infant to be monitored;

means to transilluminate the fiber means; and means to monitor the transillumination as a function of the movement of the infant and of the fiber means.

9. The apparatus as set forth in claim 8 and further including a garment with the fiber means woven into the garment so as to be located on the chest/belly region of the infant.

10. The apparatus as set forth in claim 8 and further including an alarm and means to trigger the alarm as a function of the monitored transillumination.

11. The apparatus as set forth in claim 10 and further including a transmitter and a separate remote portable alarm unit.

12. The apparatus as set forth in claim 11 wherein the signal is infrared.

13. The apparatus as set forth in claim 11 wherein the signal is ultrasound.

14. The apparatus as set forth in claim 11 wherein the signal is radiowave.

15. The apparatus as set forth in claim 11 and further including means associated with the evaluating unit and the remote alarm for transmitting therebetween a verification signal.

16. The apparatus as set forth in claim 10 wherein the alarm is optical.

17. The apparatus as set forth in claim 10 wherein the alarm is acoustical.

18. The apparatus as set forth in claim 8 wherein the fiber means is an optical monofilament.

19. The apparatus as set forth in claim 8 wherein the fiber means is a bundle of fiber optic filaments.

* * * * *

REEXAMINATION CERTIFICATE (2716th)
United States Patent [19]
Buschmann

[11] B1 5,241,300
[45] Certificate Issued Oct. 31, 1995

[54] SIDS DETECTION APPARATUS AND METHODS

[76] Inventor: Johannes Buschmann, Birkenleiten 9, 8000 München 90, Germany

Reexamination Request:
No. 90/003,388, Feb. 25, 1994

Reexamination Certificate for:
Patent No.: 5,241,300
Issued: Aug. 31, 1993
Appl. No.: 874,297
Filed: Apr. 24, 1992

[51] Int. Cl.⁶ .................................................. G08B 21/00
[52] U.S. Cl. ........................ 340/573; 128/721; 340/531; 340/600
[58] Field of Search ..................... 340/531, 573

[56] References Cited

U.S. PATENT DOCUMENTS

| | | | |
|---|---|---|---|
| 3,965,944 | 6/1976 | Goff, Jr. et al. | 139/421 |
| 4,196,425 | 4/1980 | Williams, Jr. et al. | 340/573 |
| 4,339,661 | 7/1982 | Pitt et al. | 250/227.19 |
| 4,547,804 | 10/1985 | Greenberg | 348/460 |
| 4,777,478 | 10/1988 | Hirsch et al. | 340/573 |
| 4,843,233 | 6/1989 | Jeunhomme | 250/227.19 |
| 5,212,379 | 5/1993 | Nafarrate et al. | 250/227.14 |
| 5,307,051 | 4/1994 | Sedlmayr | 340/573 |

OTHER PUBLICATIONS

Hentschel, Christian, "Numerical Aperture (NA)" *Fiber Optics Handbook*, 3 ed., pp. 145–146. Hewlett Packard, Fed. Rep. of Ger., 1989.

Bergmann–Schaeffer, *Lehrbuch der Experimentalphysik*, Band III, "Optik", pp. 28–40, Walter DeGruyter, Berlin, 1974.

Chai Yeh, *Handbook of Fiber Optics*, Cpt 3, "Wave Propagation in Lightguides", pp. 38 ff, Academic Press, Inc., Harcourt Brace Jovanovich, Publishers, New York, 1990.

Wolfbeis, Otto S., Fiber Optic Chemical Sensors and Biosensors, vol. I, "Fiber Optics Sensors", pp. 4–8, CRC Press, Boca Raton, 1991.

*Primary Examiner*—Glen R. Swann, III

[57] ABSTRACT

A transilluminated optical fiber is placed adjacent to an infant's respiratory moving parts using an elastic fabric. Use is made of the effect that moving the fiber causes a modulation of the intensity of the transmitted light to monitor the infant's breathing pattern to avoid S(udden) I(nfant) D(eath) S(yndrome).

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 4, line 49 through column 5, line 15:

According to the invention, use is made of the effect that light in optical fibers shows a change of intensity when the fiber is moved, that is to say, it shows a change of the transmission of light through the fiber. There are two reasons for the change: (1) change in the conditions of propagation for modes if use is made of coherent light and (2) change in the geometry of total reflection within the fiber. In an unmoved fiber a fixed amount of light is transmitted through the fiber by means of total reflection. On the other hand, simultaneously a fixed amount of light leaves the fiber because the condition for total reflection is not met for all light paths, for example, at bendings, especially if light is fed into the fiber using almost the full maximum acceptance angle of the fiber. The maximum acceptance angle $2\alpha$ results from the numerical aperture NA of the fiber:

$$\sin \alpha = NA = \sqrt{n_1^2 - n_2^2}$$

*where $n_1$ is the core refractive index and $n_2$ is the cladding refractive index.* If the fiber is moved, then the geometry of the fiber is also changed; that is to say the angles of reflection in the fiber change with it. Total reflection may not be possible anymore where it has been before and vice versa. Thus a change in geometry changes the ratio of transmitted to lost light in the fiber. Only in an unmoved fiber will the conditions for total reflection stay the same at every spot in the fiber. An additional change in transmission can be caused by a change of the overall length of the light path and the number of total reflections if the geometry of the fiber is changed, both altering the absorption of light. A further change in transmission results from a change of the cross section of the fiber which is slightly deformed during bending, the more the softer the material is of which the fiber is made.

AS A RESULT OF REEXAMINATION, IT HAS BEEN DETERMINED THAT:

Claims 1, 3, 8 and 11 are determined to be patentable as amended.

Claims 2, 4–7, 9, 10 and 12–19, dependent on an amended claim, are determined to be patentable.

New claims 20, 21, 22 and 23 are added and determined to be patentable.

1. A method of monitoring the respiration of an infant comprising the steps of:

placing optical fiber means adjacent to the respiratory parts of the infant to be monitored;

*feeding light into the fiber using up to the full maximum acceptance angle of the fiber, where the maximum acceptance angle of the fiber $2\alpha$ results from the numerical aperture of NA of the fiber*

$$\sin \alpha = NA = \sqrt{n_1^2 - n_2^2}$$

*where $n_1$ is the core refractive index and $n_2$ is the cladding refractive index, and* transmitting light from a light source through the fiber means onto a photoelectric converter;

monitoring changes in the intensity of the transmitted light as a function of the movement of the fiber means in response to the movement of respiratory parts of the infant;

comparing changes in the intensity of transmitted light through movement of the fiber means corresponding to the infant's respiratory effects, with a predetermined threshold, indicating whether or not the infant is breathing;

comparing the time elapsed since the last respiratory effect with a given maximum tolerable respiratory arrest time; and giving an alarm if the elapsed time exceeds the predetermined tolerable respiratory arrest time.

3. A method for monitoring the movement caused by the normal respiration of an infant and for triggering an alarm in response to the prolonged stoppage of such movement comprising the steps of:

placing an optical fiber means in a sinusoidal manner adjacent to the body of the infant to be monitored;

establishing a tight contact of a garment containing the optical fiber *with the body* by making use of an elastic fabric;

transilluminating the fiber means with a light having a wavelength of between about 0.1 and 5 μm;

monitoring the change of transmission of the fiber means *due to total reflection within the fiber* with an evaluating electronic unit as a function of the movement of the fiber means as caused by the movement of the infant's respiratory part; and triggering an alarm upon the prolonged stoppage of the movement of the infant and the fiber means.

8. Apparatus for monitoring the respiration of an infant comprising, in combination:

optical fiber means located adjacent to the body of the infant to be monitored;

means to transilluminate the fiber means *with incoherent light using up to the full maximum acceptance angle of the fiber, where the maximum acceptance angle of the fiber $2\alpha$ results from the numerical aperture of NA of the fiber*

$$\sin \alpha = NA = \sqrt{n_1^2 - n_2^2} \;;$$

*where $n_1$ is the core refractive index and $n_2$ is the cladding refractive index, and* means to monitor the transillumination as a function of the *transmitted to lost light in the fiber as a result of* change in geometry of the fiber means due to movement of the infant [and of the fiber means].

11. The apparatus as set forth in claim 10 and further including a transmitter *for transmitting a signal* and a separate remote portable alarm unit.

20. A method as in claim 1, wherein said light source is a light emitting diode (LED).

21. *A method of monitoring the respiration of an infant comprising the steps of:*

*placing optical fiber means adjacent to the respiratory parts of the infant to be monitored;*

*transmitting light from a light source through the fiber means onto a photoelectric converter;*

*producing a signal corresponding to the total transmitted light;*

*monitoring changes in the intensity of the signal corresponding to the total transmitted light as a function of the movement of the fiber means in response to the movement of respiratory parts of the infant;*

*comparing changes in the intensity of transmitted light through movement of the fiber means corresponding to the infant's respiratory effects, with a predetermined threshold, indicating whether or not the infant is breathing;*

*comparing the time elapsed since the last respiratory effect with a given maximum tolerable respiratory arrest time; and*

*giving an alarm if the elapsed time exceeds the predetermined tolerable respiratory arrest time.*

22. *A method of monitoring the respiration of an infant comprising the steps of:*

*placing optical fiber means adjacent to the respiratory parts of the infant to be monitored;*

*transmitting incoherent light from a source of incoherent light through the fiber means onto a photoelectric converter;*

*monitoring changes in the intensity of the transmitted incoherent light as a function of the movement of the fiber means in response to the movement of respiratory parts of the infant;*

*comparing changes in the intensity of transmitted incoherent light through movement of the fiber means corresponding to the infant's respiratory effects, with a predetermined threshold, indicating whether or not the infant is breathing;*

*comparing the time elapsed since the last respiratory effect with a given maximum tolerable respiratory arrest time; and*

*giving an alarm if the elapsed time exceeds the predetermined tolerable respiratory arrest time.*

23. *An article as in claim 22, wherein said source of incoherent light is a light emitting diode (LED).*

\* \* \* \* \*